US009986922B2

(12) United States Patent
Uchida et al.

(10) Patent No.: US 9,986,922 B2
(45) Date of Patent: Jun. 5, 2018

(54) PULSE WAVE DETECTION METHOD, PULSE WAVE DETECTION APPARATUS, AND RECORDING MEDIUM

(71) Applicant: FUJITSU LIMITED, Kawasaki-shi, Kanagawa (JP)

(72) Inventors: Daisuke Uchida, Atsugi (JP); Masato Sakata, Isehara (JP); Hidenori Sekiguchi, Hadano (JP); Akihiro Inomata, Atsugi (JP)

(73) Assignee: FUJITSU LIMITED, Kawasaki (JP)

( * ) Notice: Subject to any disclaimer, the term of this patent is extended or adjusted under 35 U.S.C. 154(b) by 484 days.

(21) Appl. No.: 14/638,570

(22) Filed: Mar. 4, 2015

(65) Prior Publication Data
US 2015/0173630 A1  Jun. 25, 2015

Related U.S. Application Data

(63) Continuation of application No. PCT/JP2012/072990, filed on Sep. 7, 2012.

(51) Int. Cl.
*A61B 5/024* (2006.01)
*A61B 5/00* (2006.01)

(52) U.S. Cl.
CPC ........ *A61B 5/02416* (2013.01); *A61B 5/0059* (2013.01); *A61B 5/024* (2013.01);
(Continued)

(58) Field of Classification Search
CPC ... A61B 5/0059; A61B 5/024; A61B 5/02416; A61B 5/7203; A61B 5/7257; A61B 5/7275; A61B 2576/00
(Continued)

(56) References Cited

U.S. PATENT DOCUMENTS 5,200,828 A * 4/1993 Jang .................. H04N 5/23212
348/345
5,431,170 A 7/1995 Mathews
(Continued)

FOREIGN PATENT DOCUMENTS

JP  05-506802   10/1993
JP  2003-135434  5/2003
(Continued)

OTHER PUBLICATIONS

Lewandowska et al., "Measuring Pulse Rate with a Webcam—a Non-contact Method for Evaluating Cardiac Activity", Proceedings of the Federated Conference on Computer Science and Information Systems, 2011, pp. 405-410.*
(Continued)

*Primary Examiner* — Christopher A Flory
(74) *Attorney, Agent, or Firm* — Fujitsu Patent Center

(57) ABSTRACT

A pulse wave detection method includes obtaining an image obtained by photographing a subject with an imaging device, extracting intensities representative of signal components of a specific frequency band for respective wavelength components among signals of a plurality of wavelength components included in the image, calculating, using the intensities extracted for the respective wavelength components, a weight coefficient by which a signal is multiplied when the signals are calculated between the wavelength components to minimize an arithmetic value of the signal components in the specific frequency band after multiplication, multiplying at least one of the signals of the respective wavelength components by the weight coefficient, performing arithmetic operation on the signals between the wavelength components after multiplication by the weight coefficient, and detecting pulse waves of the subject using a signal after the arithmetic operation.

10 Claims, 9 Drawing Sheets

(52) U.S. Cl.
CPC .......... *A61B 5/7203* (2013.01); *A61B 5/7257* (2013.01); *A61B 5/7275* (2013.01); *A61B 2576/00* (2013.01)

(58) Field of Classification Search
USPC ........................................................ 600/479
See application file for complete search history.

(56) References Cited

U.S. PATENT DOCUMENTS

| | | | |
|---|---|---|---|
| 5,632,272 | A | 5/1997 | Diab et al. |
| 6,081,735 | A | 6/2000 | Diab et al. |
| 6,157,850 | A | 12/2000 | Diab et al. |
| 6,236,872 | B1 | 5/2001 | Diab et al. |
| 6,616,611 | B1* | 9/2003 | Moehring ................ A61B 8/06 600/441 |
| 8,795,173 | B2* | 8/2014 | Poh ..................... A61B 5/02405 600/301 |
| 2003/0083583 | A1 | 5/2003 | Kovtun et al. |
| 2003/0122954 | A1* | 7/2003 | Kassatly ............. H04N 5/2254 348/335 |
| 2005/0075553 | A1 | 4/2005 | Sakai et al. |
| 2006/0244842 | A1* | 11/2006 | Hatano ................. H04N 9/045 348/223.1 |
| 2009/0043210 | A1 | 2/2009 | Kitoh et al. |
| 2010/0016732 | A1* | 1/2010 | Wells .................... A61B 5/0059 600/476 |
| 2010/0268056 | A1* | 10/2010 | Picard ................. A61B 5/0531 600/388 |
| 2010/0324384 | A1* | 12/2010 | Moon .................. A61B 5/1118 600/323 |
| 2010/0324389 | A1* | 12/2010 | Moon .................. A61B 5/1118 600/324 |
| 2011/0054336 | A1 | 3/2011 | Jornod |
| 2011/0251493 | A1* | 10/2011 | Poh ..................... G06K 9/00255 600/477 |
| 2011/0256631 | A1* | 10/2011 | Tomaney ............. C12Q 1/6869 436/94 |
| 2012/0179011 | A1* | 7/2012 | Moon .................. A61B 5/7207 600/324 |
| 2012/0195473 | A1 | 8/2012 | De Haan et al. |
| 2015/0099987 | A1* | 4/2015 | Bhatkar ................ A61B 5/165 600/479 |

FOREIGN PATENT DOCUMENTS

| | | |
|---|---|---|
| JP | 2005-160640 | 6/2005 |
| JP | 2005-185834 | 7/2005 |
| JP | 2005-218507 | 8/2005 |
| JP | 2009-297234 | 12/2009 |
| JP | 2010-264095 | 11/2010 |
| JP | 2011-050745 | 3/2011 |
| JP | 2011-130996 | 7/2011 |
| WO | 1991-018550 | 12/1991 |
| WO | 1996-012435 | 5/1996 |
| WO | 2007-043328 | 4/2007 |
| WO | 2010/100594 A2 | 9/2010 |

OTHER PUBLICATIONS

EESR—Extended European Search Report of European Patent Application No. 12884118.6 dated Aug. 25, 2015.
Ming-Zher Poh et al: "Non-contact, automated cardiac pulse measurements using video imaging and blind source separation", Optic Express, vol. 18, No. 10, May 10, 2010. pp. 10762. XP055016649.
CNOA—Notification of the First Office Action dated Jan. 21, 2016 for corresponding Chinese Application No. 201280075664.3 , with English translation of the relevant part.
Poh et al.,"Non-contact, automated cardiac pulse measurements using video imaging and blind source separation.", Optics Express, May 10, 2010, pp. 10763-10775, vol. 18 No. 10, Optical Society of America. [14 pages] [Cited in the above listed CNOA].
International Search Report, mailed in connection with PCT/JP2012/072990 dated Oct. 16, 2012.

* cited by examiner

PULSE WAVE DETECTION METHOD, PULSE WAVE DETECTION APPARATUS, AND RECORDING MEDIUM

CROSS-REFERENCE TO RELATED APPLICATION

This application is a continuation application of International Application PCT/JP2012/072990 filed on Sep. 7, 2012 and designating the U.S., the entire contents of which are incorporated herein by reference.

FIELD

The embodiments discussed herein are directed to a pulse wave detection method, a pulse wave detection apparatus, and a pulse wave detection program.

BACKGROUND

There are known methods of detecting fluctuations of the volume of the blood, that is, pulse waves, from an image obtained by imaging a subject. Generally, improvement in detection accuracy is attempted by photographing an image using a light source such as infrared light or photographing an image with an imaging device in close contact with the living body of the subject. However, such a case has demerits such as providing hardware such as a light source and bringing a measurement tool into contact with a living body.

For this reason, it is desired to detect pulse waves without contact between the measurement tool and the living body under environmental light such as sunlight and indoor light. However, the measurement of pulse waves without infrared light or the like incurs large influence of noise, which can possibly decrease the accuracy of detection of pulse waves.

For example, the following signal processor has been presented as an example of a technique for reducing noise. The signal processor is provided with a light-emitting diode that emits red wavelength light and a light-emitting diode that emits infrared wavelength light. With this structure, the signal processor determines a coefficient that minimizes correlation between respective signals obtained by transmission rays of the two light-emitting diodes, and removes a noise component from one signal of the signals using the other signal multiplied by the coefficient. In this processing, the signal processor comprehensively calculates correlation for each of n assumed values, to use the assumed value with the least correlation as a coefficient.

Patent Literature 1: Japanese Laid-open Patent Publication No. 2003-135434
Patent Literature 2: Japanese Laid-open Patent Publication No. 2005-185834
Patent Literature 3: Japanese Laid-open Patent Publication No. 2005-218507

However, the above conventional art increases the processing load because calculation is performed n times to derive a coefficient for reducing noise. In addition, when the number n of the assumed values is reduced to prevent an increase in processing load, the coefficient is diverged from a proper value, which reduces the accuracy of detection of pulse waves.

SUMMARY

According to an aspect of the embodiment of the invention, a pulse wave detection method includes obtaining an image obtained by photographing a subject with an imaging device, extracting intensities representative of signal components of a specific frequency band for respective wavelength components among signals of a plurality of wavelength components included in the image, the specific frequency band having a section having a predetermined length or less overlapping a frequency band that pulse waves are enabled to take, calculating, using the intensities extracted for the respective wavelength components, a weight coefficient by which a signal is multiplied when the signals are calculated between the wavelength components to minimize an arithmetic value of the signal components in the specific frequency band after multiplication, multiplying at least one of the signals of the respective wavelength components by the weight coefficient, performing arithmetic operation on the signals between the wavelength components after multiplication by the weight coefficient, and detecting pulse waves of the subject using a signal after the arithmetic operation.

The object and advantages of the invention will be realized and attained by means of the elements and combinations particularly pointed out in the claims.

It is to be understood that both the foregoing general description and the following detailed description are exemplary and explanatory and are not restrictive of the invention.

DESCRIPTION OF EMBODIMENTS

Preferred embodiments of the pulse wave detection method, the pulse wave detection apparatus, and the pulse wave detection program disclosed in the present application will be explained in detail with reference to the accompanying drawings. The embodiments do not restrict the disclosed technique. The embodiments may be properly combined within the range in which the details of the processes do not conflict with each other.

First Embodiment

Figure 1:
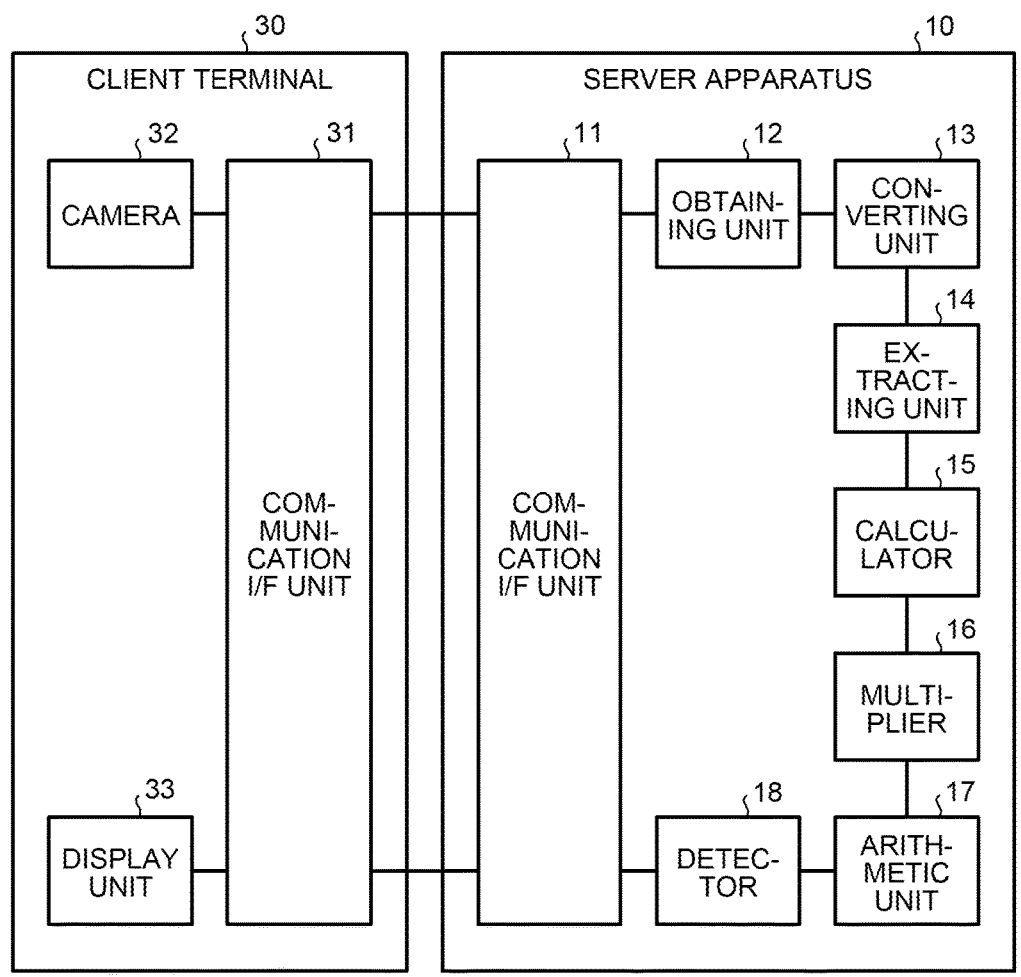
FIG. 1 is a block diagram illustrating a functional configuration of devices included in a pulse wave detection system according to a first embodiment.

FIG. 1 is a block diagram illustrating a functional configuration of devices included in a pulse wave detection system according to a first embodiment. A server apparatus 10 illustrated in FIG. 1 provides the pulse wave detection service of detecting pulse waves of a subject using an image obtained by photographing the subject, without contact between the measurement tool and the living body, under environmental light such as sunlight and indoor light. The term "pulse waves" indicates an index indicating fluctuations of the volume of the blood, that is, increases and decreases in the blood flow, and includes the heart rate and the heart beat waveform.

A form of the server apparatus 10 can be mounted by installing an electronic medical chart program that provides an electronic medical chart service as packaged software or on-line software in a desired computer. For example, the server apparatus 10 may be mounted as a Web server that provides the above pulse wave detection service, or a cloud that provides the above pulse wave detection service by outsourcing.

As illustrated in FIG. 1, the server apparatus 10 and a client terminal 30 are connected via a desired network, to be enabled to perform communication with each other. A communication network of a desired type may be adopted as the network, such as the Internet, a local area network (LAN), and a VPN (virtual private network). Although the example of FIG. 1 illustrates the case where one client terminal 30 is connected to the server apparatus 10, a plurality of client terminals may be connected to the server apparatus 10.

Configuration of Client Terminal 30

The client terminal 30 is a terminal device that is provided with the pulse wave detection service provided by the server apparatus 10. A form of the client terminal 30 is a fixed terminal such as a personal computer, or a mobile terminal such as a mobile phone, a personal handyphone system (PHS), and personal digital assistants (PDA).

The client terminal 30 includes a communication interface (I/F) unit 31, a camera 32, and a display unit 33, as illustrated in FIG. 1. The client terminal 30 may include various functional units included in a known computer, such as an antenna, a carrier communication unit that performs communication via a carrier network, and a global positioning system (GPS) receiver, as well as the functional units illustrated in FIG. 1.

Among the functional units, the communication I/F unit 31 is an interface that controls communication with another device, such as the server apparatus 10. A network interface card such as a LAN card may be adopted as a form of the communication I/F unit 31. For example, the communication I/F unit 31 transmits an image obtained by photographing the subject's face with the camera 32 to the server apparatus 10, and receives a pulse wave detection result from the server apparatus 10.

The camera 32 is an imaging device using an imaging device such as a charge coupled device (CCD) and a complementary metal oxide semiconductor (CMOS). For example, the camera 32 may be provided with light-receiving elements of three type or more, such as red (R), green (G), and blue (B). As an example of mounting the camera 32, a digital camera or a Web camera may be connected via an external terminal, or a camera mounted on a device such as a mobile terminal in shipping may be used. Although the example illustrates the case where the client terminal 30 includes the camera 32, the client terminal 30 does not necessarily include the camera 32 when an image can be obtained via the network or a storage device.

The display unit 33 is a display device that displays various pieces of information, such as a pulse wave detection result transmitted from the server apparatus 10. As a form of the display unit 33, a monitor or a display can be adopted, or the display unit 33 may be mounted as a touch panel formed as one unitary piece with the input unit. The display unit 33 may be omitted, when no information is displayed through the client terminal 30. The information may be displayed on a display unit of another client terminal 30 or the like.

The client terminal 30 includes a pre-installed or installed application program that is provided with the pulse wave detection service from the server apparatus 10 in cooperation with the server apparatus 10. The above client application program may be referred to as "client application" hereinafter.

When the client application is started up via an input device that is not illustrated, the client application starts up the camera 32. In response to the startup, the camera 32 starts photographing the subject contained in the photographing range of the camera 32. In photographing, the client application can display a target position reflecting the subject's nose as a sight, while displaying the image photographed by the camera 32 on the display unit 33. This display enables the photographing of an image in which the subject's nose is contained in the central part of the photographing range among the subject's facial parts such as the eyes, ears, nose, and mouth. The client application transmits the image obtained by photographing the subject's face with the camera 32 to the server apparatus 10 via the communication I/F unit 31. Next, when the client application receives a pulse wave detection result from the server apparatus 10, such as the subject's heart rate and heart beat waveform, the client application displays the subject's heart rate and heart beat waveform on the display unit 33.

Configuration of Server Apparatus 10

By contrast, the server apparatus 10 includes a communication I/F unit 11, an obtaining unit 12, a converting unit 13, an extracting unit 14, a calculator 15, a multiplier 16, an arithmetic unit 17, and a detector 18, as illustrated in FIG. 1. The server apparatus 10 may include various functional units included in a known server apparatus, such as various input/output devices, as well as the functional units illustrated in FIG. 1.

Among the functional units, the communication I/F unit 11 is an interface that controls communication with another device, such as the client terminal 30. A network interface card such as a LAN card may be adopted as a form of the communication I/F unit 11. For example, the communication I/F unit 11 receives an image obtained by photographing the subject's face from the client terminal 30, and transmits a pulse wave detection result to the client terminal 30.

The obtaining unit 12 is a processor that obtains an image obtained by photographing the subject. As a form, the obtaining unit 12 obtains an image photographed with the camera 32 of the client terminal 30. As another form, the obtaining unit 12 is capable of obtaining an image from an auxiliary storage device such as a hard disk and an optical disk storing therein images obtained by photographing the subject, or a removable medium such as a memory card and a universal serial bus (USB) memory. The image obtained by the obtaining unit 12 as described above is output to the extracting unit 14. The obtaining unit 12 can intermittently or continuously obtain still images including the subject, or obtain a stream of video encoded data encoded by a predetermined compression encoding method. Although the example illustrates the case where the obtaining unit 12 executes processing using image data such as two-dimensional bitmap data or vector data obtained from an output of an imaging device such as a CCD and a CMOS, a signal that is output from a detector may be obtained as it is to execute the subsequent processing.

In addition, the obtaining unit 12 extracts a partial image based on a predetermined facial part from the image obtained by photographing the subject's face. As a form, the obtaining unit 12 executes image processing such as template matching on the image including the subject's face, to detect a specific facial part, that is, the subject's nose among the subject's facial parts such as the eyes, ears, nose, and mouth. Next, the obtaining unit 12 extracts a partial part included in a predetermined range including the center with the subject's nose serving as the center. This operation extracts a partial image including the facial center part including the subject's nose and part of the cheeks located around the nose, as the image used for detection of pulse waves. Thereafter, the obtaining unit 12 outputs the partial image extracted from the original image to the converting unit 13.

Figure 2:
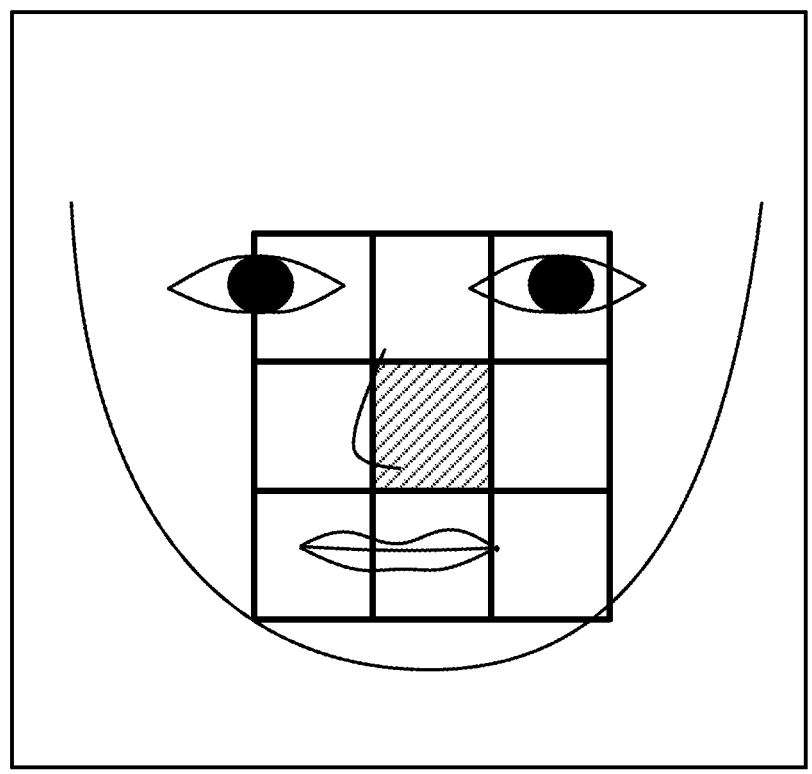
FIG. 2 is a diagram illustrating an example of an image including the face of a subject.

FIG. 2 is a diagram illustrating an example of the image including the subject's face. FIG. 2 illustrates nine blocks obtained by dividing a region including part or whole of the subject's eyes, nose, and mouth included in the image. Among the blocks illustrated in FIG. 2, the upper left and right blocks include the subject's eyes. When images of these blocks are used for detection, blinks of the eyes may serve as noise that causes a decrease in the accuracy of detection of the heart rate. Among the blocks illustrated in FIG. 2, the lower three blocks include the subject's mouth. When images of these blocks are used for detection, the movement of a mouth may serve as noise that causes a decrease in the accuracy of detection of the heart rate. By contrast, the center middle block illustrated in FIG. 2, that is, the block painted with diagonal lines is separated from the blocks including the eyes or the mouth. Accordingly, the center middle block has lower possibility of including a component serving as noise than those of the other blocks, and the center middle block can be expected to produce a better detection result. For these reasons, the obtaining unit 12 extracts an image of the center middle block illustrated in FIG. 2 as a partial image from the original image.

The converting unit 13 is a processor that converts each two or more wavelength components included in the partial image into frequency components. The present embodiment illustrates the case where pulse waves are detected using signals of two wavelength components formed of R component and G component among the R component, the G component, and the B component. Specifically, a G signal having a light wavelength of 525 nm band has a higher light absorption sensitivity than that of the other components. In the present embodiment, such a G component is used as a basis and used together with signals of other light wavelengths, such as a signal that has passed through a band stop filter, as well as an R signal and a B signal, to cancel the noise component.

As a form, whenever a partial image is input from the obtaining unit 12, the converting unit 13 calculates a mean value of pixel values of the pixels included in the partial image for each of the R component and the G component included in the partial image. Next, when the mean value of each component of the partial image is sampled in a time-series manner for a predetermined time such as one second and one minute, the converting unit 13 performs discrete Fourier transform (DFT) on the signals of the sampled R component and the sampled G component. By performing such DFT, the R signal and the G signal are converted into respective frequency spectrums. The respective frequency spectrums obtained for the R signal and the G signal by application of DFT are output to the extracting unit 14. Although this example illustrates the case of applying discrete Fourier transform, another method may be applied as long as the method is capable of developing a signal into frequency components. For example, the disclosed device can use Fourier transform, fast Fourier transform (FFT), or discrete cosine transform (DCT), as well as discrete Fourier transform.

The extracting unit 14 is a processor that extracts a signal intensity representative of a signal component of a specific frequency band having a section of a predetermined length or less that overlaps the frequency band that pulse waves can take, for each wavelength component, from the frequency spectrum of each wavelength component.

The term "specific frequency band" indicates a frequency band in which a noise component markedly appears in comparison with other frequency bands. For example, a specific frequency band can be defined by comparing the frequency band with a frequency band that pulse waves can take. An example of the frequency band that pulse waves can take is a frequency band equal to or larger than 0.7 Hz and less than 4 Hz, that is, a frequency band equal to or larger than 42 bpm and equal to or less than 240 bpm when it is converted into a frequency band per minute. In view of the above, an example of the specific frequency band can be a frequency band less than 0.7 Hz and equal to or larger than 4 Hz, which may not be measured as pulse waves. Part of the specific frequency band may overlap the frequency band that pulse waves can take. For example, the specific frequency band may be allowed to overlap the frequency band that pulse waves can take in a section of 0.7 Hz to 1 Hz that is hardly supposed to be measured as pulse waves that can take a frequency band less than 1 Hz and equal to or larger than 4 Hz as the specific frequency band.

Such specific frequency band may be narrowed to a frequency band in which noise appears more markedly and having a frequency band less than 1 Hz and equal to or larger than 4 Hz as an outer edge. For example, noise appears more markedly in a low frequency band lower than the frequency band that pulse waves can take, than a high frequency band higher than the frequency band that pulse waves can take. For this reason, the specific frequency band can be narrowed to a frequency band less than 1 Hz. In addition, the specific frequency band may be narrowed to a frequency band equal to or larger than 3 bpm and less than 1 Hz because most difference in sensitivity between the imaging devices of the respective components is included in the vicinity of a direct-current component having a zero spatial frequency. The specific frequency band may also be narrowed to a frequency band equal to or larger than 3 bpm and less than 20 bpm, in which noise easily occurs, such as the movement of a human body such as blinks and body shake, and flicker of the environmental light.

As a form, the extracting unit 14 extracts a signal intensity representative of the signal component in the specific frequency band for each of the R component and the G component. As an example, the extracting unit 14 is capable of extracting a signal intensity corresponding to a preset frequency in the frequency band equal to or larger than 3 bpm and less than 20 bpm. As another example, the extracting unit 14 is capable of extracting a mean value of the signal intensities by executing averaging such as arithmetic mean, weighted mean, and moving average on the signal intensities in the frequency band equal to or larger than 3 bpm and less than 20 bpm, and extracting an integrated value of the signal intensities by integrating the signal intensities. In the following explanation, the signal intensity representative of the signal component being the R component in the specific frequency band may be referred to as "$R_{noise}$", and the signal intensity representative of the signal component being the G component in the specific frequency band may be referred to as "$G_{noise}$".

Figure 3:
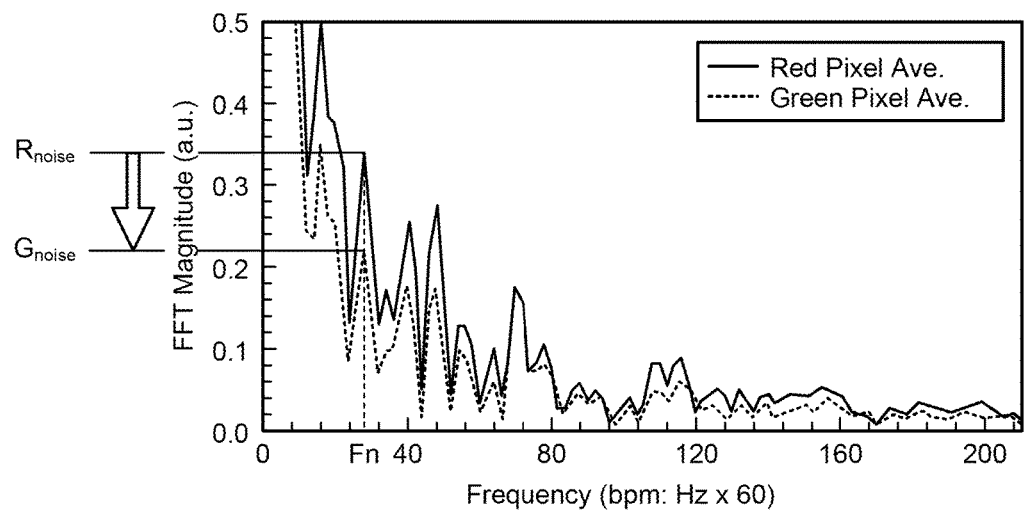
FIG. 3 is a diagram illustrating an example of signal intensities representative of signal components in a specific frequency band in an R component and a G component.

FIG. 3 is a diagram illustrating an example of signal intensities representative of the signal components being the R component and the G component in the specific frequency band. The vertical axis of the graph illustrated in FIG. 3 indicates the signal intensity and the horizontal axis indicates the frequency (bpm). As illustrated in FIG. 3, the signal intensities of the R component and the G component are different from each other because they are different in sensitivity of the imaging device. By contrast, the R component and the G component are the same in that noise occurs in the specific frequency band equal to or larger than 3 bpm and less than 20 bpm. For this reason, in the example of FIG. 3, the signal intensities corresponding to a designated frequency $F_n$ included in the specific frequency band equal to or larger than 3 bpm and less than 20 bpm are extracted as $R_{noise}$ and $G_{noise}$.

The calculator 15 is a processor that calculates, using the signal intensities extracted for the respective wavelength components by the extracting unit 14, a weight coefficient by which one signal is multiplied when the signals are calculated between the wavelength components. The weight coefficient minimizes the arithmetic value of the signal component of the specific frequency band after multiplication.

As a form, the calculator 15 calculates a weight coefficient that minimizes the arithmetic value of the signal intensities in the specific frequency band between the R component and the G component. For example, the calculator 15 calculates coefficients $a_1$ and $a_2$ that satisfy the derivation expression "$a_1*R_{noise}+a_2*G_{noise}=0$". These coefficients $a_1$ and $a_2$ cancel the signal intensities in the specific frequency band corresponding to noise among signal intensities that are different between the respective components, to make the signal intensities uniform, without attenuating the difference therebetween in signal intensity around the frequency in which pulse waves strongly appear so much as the components corresponding to noise in the specific frequency band. Either of the values of the coefficients $a_1$ and $a_2$ takes a negative value. Next, the calculator 15 calculates a weight coefficient $a_1/a_2$ for the spectrum of the R signal, and a weight coefficient $a_2/a_2$ for the spectrum of the G signal.

Figure 4:
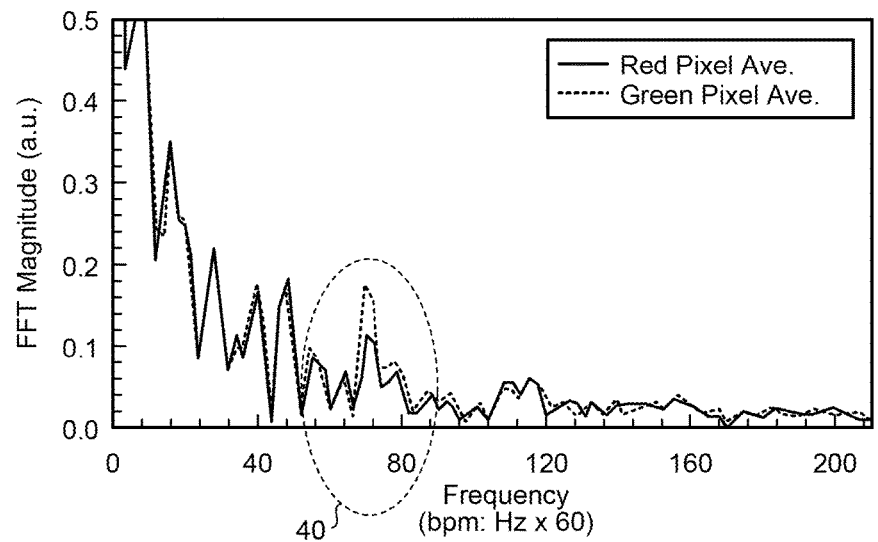
FIG. 4 is a diagram illustrating an example of spectrums of signals of an R component and a G component multiplied by a weight coefficient.

The multiplier 16 is a processor that multiplies at least one signal component of the signals of the wavelength components by the weight coefficient. As a form, the multiplier 16 multiplies the spectrum of each signal of the R component and the G component by the weight coefficient. In the above example, the multiplier 16 multiplies the spectrum $R_{all}$ of the R signal by the weight coefficient $a_1/a_2$, and multiplies the spectrum $G_{all}$ of the G signal by the weight coefficient $a_2/a_2$. FIG. 4 is a diagram illustrating an example of spectrums of signals of the R component and the G component multiplied by the weight coefficient. The example of FIG. 4 illustrates a result of multiplication by the absolute value of the weight coefficient, for the convenience of explanation. The vertical axis of the graph illustrated in FIG. 4 indicates the signal intensity, and the horizontal axis indicates the frequency (bpm). As illustrated in FIG. 4, when the spectrums of the signals of the R component and the G component are multiplied by the respective weight coefficients, the sensitivities are made uniform between the components of the R component and the G component. In particular, most parts of the signal intensities of the spectrums are substantially identical in the specific frequency band. By contrast, in a surrounding region 40 around the frequency in which pulse waves are actually included, the signal intensities of the spectrums are not uniform between the components of the R component and the G component.

Figure 5:
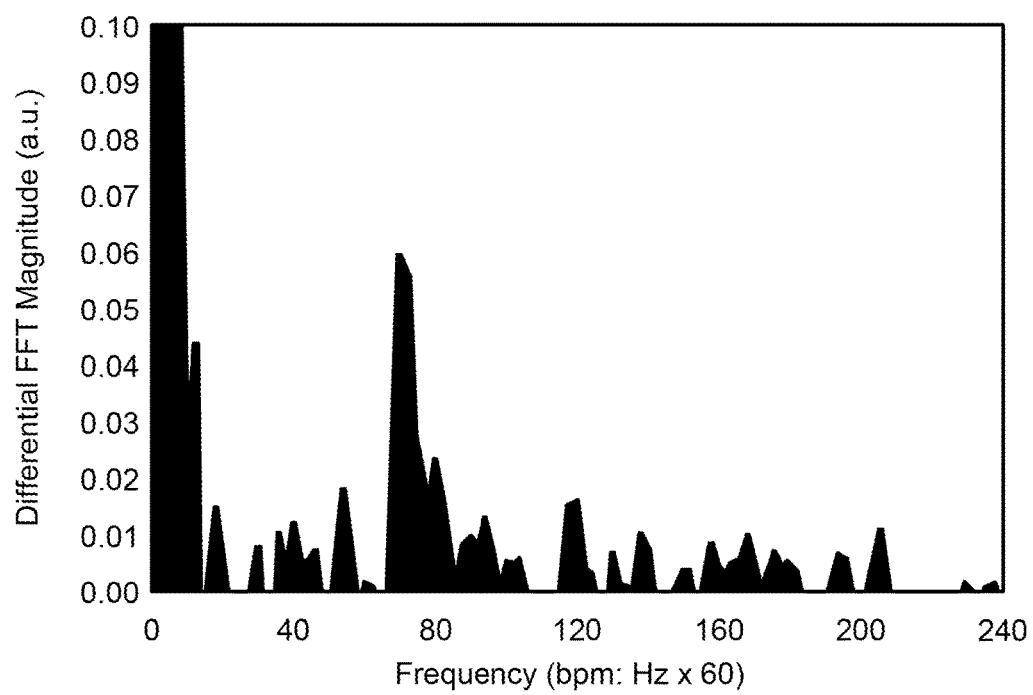
FIG. 5 is a diagram illustrating an example of a spectrum after multiplication.

The arithmetic unit 17 is a processor that performs arithmetic operation on signals between the wavelength components after multiplication by the weight coefficients. As a form, the arithmetic unit 17 performs arithmetic operation between a multiplication result of the spectrum $R_{all}$ of the R signal and the weight coefficient $a_1/a_2$, and a multiplication result of the spectrum $G_{all}$ of the G signal and the weight coefficient $a_2/a_2$. In this case, because the weight coefficient $a_1/a_2$ is negative, the spectrum of the R signal after multiplication by the weight coefficient is subtracted from the spectrum of the G signal after multiplication by the weight coefficient. FIG. 5 is a diagram illustrating an example of the spectrum after the arithmetic operation. FIG. 5 illustrates the signal intensity serving as the vertical axis in a large scale from the viewpoint of increasing the visibility of the frequency band in which pulse waves appear. FIG. 5 illustrates that the noise component is reduced in a state where the intensity of the signal component in which pulse waves appear is maintained as much as possible, in the case where the spectrum of the R signal after multiplication by the weight coefficient is subtracted from the spectrum of the G signal after multiplication by the weight coefficient. This structure enables the detection of the peak that exists around 70 bpm from the spectrum serving as the difference between them, without being mixed with the peak of the noise component.

The detector 18 is a processor that detects pulse waves of the subject using the spectrum after arithmetic operation. As a form, the detector 18 detects the subject's heart rate from the maximum peak of the spectrum after arithmetic operation in a frequency section corresponding to the section having the lower limit value of 42 bpm and the upper limit value of 240 bpm. For example, in the example of FIG. 5, as the maximum peak in the spectrum after arithmetic operation is measured at 70 bpm, the detector 18 detects the subject's heart rate as "70 bpm". As another form, the detector 18 applies inverse Fourier transform to the spectrum after arithmetic operation, to convert the frequency component of the spectrum into a time-series spatial signal. The heart beat waveform is obtained by such inverse Fourier transform.

The detection result detected as described above, such as the heart rate and the heart beat waveform, can be output to the client terminal 30, for example. In output, the detector 18 outputs the subject's heart rate to a diagnostic program that diagnoses whether the subject suffers from a heart disease, for example, a Web application mounted on the server apparatus 10. The detector 18 may also output a diagnostic result obtained by causing the diagnostic program to diagnose the subject's heart diagnose to the client terminal 30 together with the heart rate. For example, the diagnostic program diagnoses that the subject is suspected to suffer from angina pectoris or myocardinal infarction when the subject with high blood pressure has tachycardia of, for example, 100 bpm or more. The diagnostic program also diagnoses arrhysmia and mental diseases, such as strains and stresses, using the heart rate. Output of such diagnostic result together enables monitoring services outside the hospital, such as those at home and at desk.

Various integrated circuits or electronic circuits may be adopted as the obtaining unit 12, the converting unit 13, the extracting unit 14, the calculator 15, the multiplier 16, the arithmetic unit 17, and the detector 18. For example, examples of the integrated circuits are an application specific integrated circuit (ASIC) and a field programmable gate array (FGPA). Examples of the electronic circuits are a central processing unit (CPU) and a micro processing unit (MPU).

Flow of Process

Figure 6:
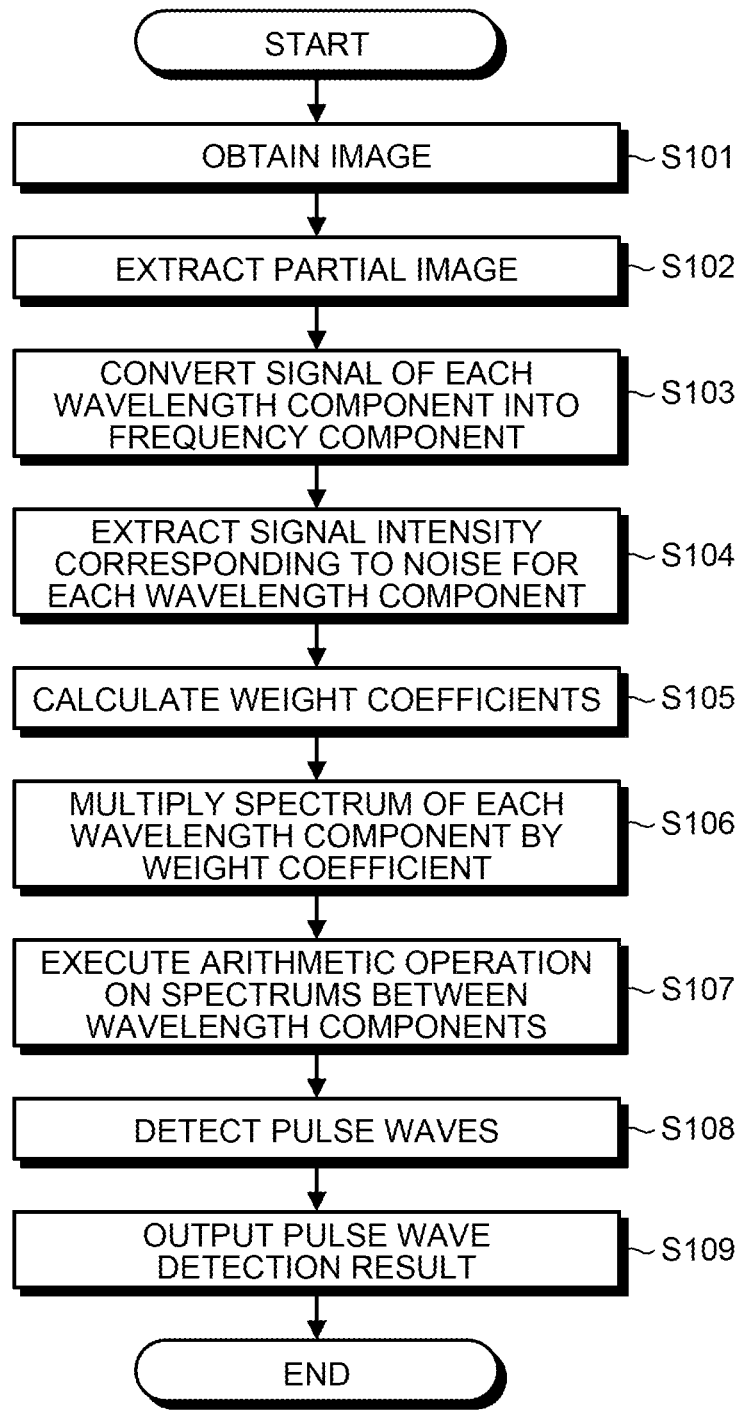
FIG. 6 is a flowchart illustrating procedures of a detection process according to the first embodiment.

Next, the flow of the process executed by the server apparatus 10 according to the present embodiment will be explained hereinafter. FIG. 6 is a flowchart illustrating procedures of a detection process according to the first embodiment. The detection process is a process that is executed repeatedly whenever an image is obtained in a state where the server apparatus 10 is turned on.

As illustrated in FIG. 6, when an image including the subject is obtained (step S101), the obtaining unit 12 extracts a predetermined facial part, such as a partial image including the subject's nose serving as a basis, from the image obtained at Step S101 (Step S102).

Next, the converting unit 13 applies discrete Fourier transform to each signal of the R component and the G component to convert them into frequency components (Step S103). In this manner, the R signal and the G signal are converted into frequency spectrums.

Next, the extracting unit 14 extracts signal intensities $R_{noise}$ and $G_{noise}$ representative of the signal components of the specific frequency band from the frequency spectrums of the respective wavelength components (Step S104). The calculator 15 calculates the weight coefficients $a_1/a_2$ and $a_2/a_2$ that minimize the arithmetic values of the signal intensities $R_{noise}$ and $G_{noise}$ in the specific frequency band between the R component and the G component (Step S105).

Thereafter, the multiplier 16 multiplies the spectrum $R_{all}$ of the R signal by the weight coefficient $a_1/a_2$, and multiplies the spectrum $G_{all}$ of the G signal by the weight coefficient $a_2/a_2$ (step S106). Next, the arithmetic unit 17 performs arithmetic operation between the multiplication result of the spectrum $R_{all}$ of the R signal and the weight coefficient $a_1/a_2$, and the multiplication result of the spectrum $G_{all}$ of the G signal and the weight coefficient $a_2/a_2$ (Step S107).

Next, the detector 18 detects pulse waves such as the subject's heart rate and heart rate waveform using the spectrum after multiplication (Step S108), thereafter outputs a pulse wave detection result to the client terminal 30 (Step S109), and ends the process.

Effect of First Embodiment

As described above, the server apparatus 10 according to the present embodiment calculates a noise intensity of a frequency component that does not substantially include any pulse waves between signals of a plurality of wavelength components, and detects pulse waves from a signal calculated by multiplying the signals of the respective wavelength components by the respective weight coefficients that minimize the arithmetic value of the noise intensity. With this structure, the server apparatus 10 according to the present embodiment enables reduction in the calculation quantity of the weight coefficients. For this reason, the server apparatus 10 according to the present embodiment enables the suppression of an increase in processing load or a decrease in accuracy when noise is reduced.

Second Embodiment

Although the first embodiment described above illustrates the example in which the noise component is canceled in the frequency space to detect pulse waves, the disclosed apparatus can cancel the noise component to detect pulse waves, without necessarily converting the signals of the respective wavelength components into frequency components. Accordingly, the present embodiment illustrates the case where the noise component is canceled in a time-series space to detect pulse waves.

Figure 7:
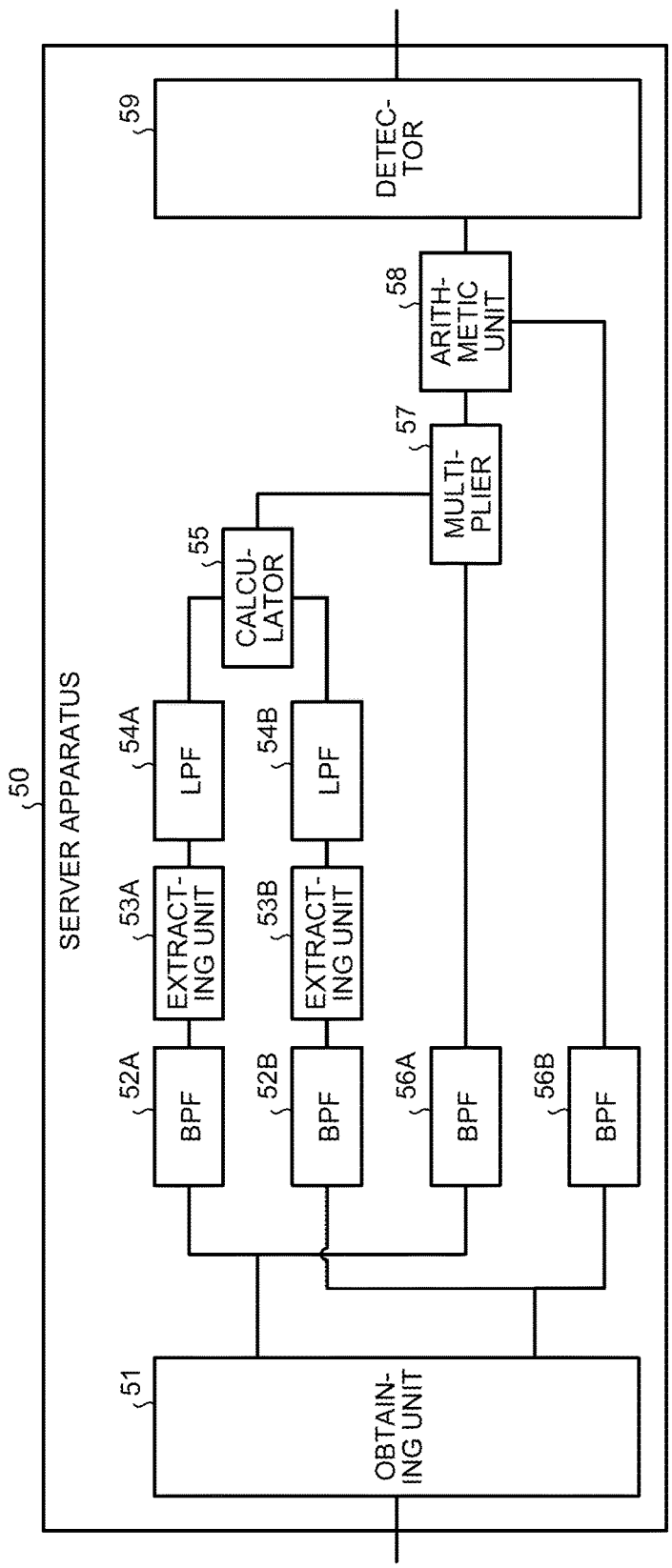
FIG. 7 is a block diagram illustrating a functional configuration of a server apparatus according to a second embodiment.

FIG. 7 is a block diagram illustrating a functional configuration of a server apparatus 50 according to a second embodiment. As illustrated in FIG. 7, the server apparatus 50 includes an obtaining unit 51, band-pass filters (BPF) 52A and 52B, extracting units 53A and 53B, low-pass filters (LPF) 54A and 54B, a calculator 55, BPFs 56A and 56B, a multiplier 57, an arithmetic unit 58, and a detector 59. The example of FIG. 7 omits illustration of the communication I/F unit.

Among the functional units, the obtaining unit 51 calculates a mean value of pixel values of pixels included in a partial image for each of the R component and the G component included in the partial image, whenever a partial image is extracted. The obtaining unit 51 also samples a mean value of each of the R signal and the G signal included in the partial image in time series for a predetermined time, such as one second and one minute, to output time-series data of the sampled R signal and the sampled G signal to the following functional unit. For example, the obtaining unit 51 outputs the time-series data of the R signal to the BPF 52A and the BPF 56A, and outputs the time-series data of the G signal to the BPF 52B and the BPF 56B.

Each of the BPF 52A, the BPF 52B, the BPF 56A, and the BPF 56B is a band-pass filter that passes only a signal component of a predetermined frequency band therethrough, and removes signal components of frequency bands other than the predetermined frequency band. The BPF 52A, the BPF 52B, the BPF 56A, and the BPF 56B may be mounted with hardware or software.

The following is explanation of difference in frequency band signals of which the BPFs pass therethrough. The BPF 52A and BPF 52B pass signal components of the specific frequency band therethrough, for example, a frequency band equal to or larger than 3 bpm and less than 20 bpm. Although this explanation illustrates the case of using band-pass filters to extract signal components of the specific frequency band, low-pass filters may be used in the case of extracting a signal component in a frequency band less than 20 bpm. By contrast, the BPF 56A and the BPF 56B pass signal components of the frequency band that pulse waves can take, for example, the frequency band equal to or larger than 42 bpm and less than 240 bpm. In the following explanation, the frequency band that pulse waves can take may be referred to as "pulse wave frequency band".

The extracting unit 53A extracts the absolute intensity value of the signal component of the R signal in the specific frequency band. For example, the extracting unit 53A extracts the absolute intensity value of the signal component of the specific frequency band, by executing a multiplication process of exponentiating the signal component of the R component in the specific frequency band. The extracting unit 53B extracts the absolute intensity value of the signal component of the G signal in the specific frequency band. For example, the extracting unit 53B extracts the absolute intensity value of the signal component of the specific frequency band, by executing a multiplication process of exponentiating the signal component of the G component in the specific frequency band.

Each of the LPF 54A and the LPF 54B is a low-pass filter that executes smoothing on time-series data of the absolute intensity value in the specific frequency band to respond to time change. The LPF 54A and the LPF 54B have no difference between them except that the signal that is input to the LPF 54A is an R signal and the signal that is input to the LPF 54B is a G signal. Such smoothing produces absolute value intensities $R'_{noise}$ and $G'_{noise}$ in the specific frequency band.

The calculator 55 calculates a weight coefficient a by executing division "$G'_{noise}/R'_{noise}$" in which the absolute value intensity $G'_{noise}$ of the G signal in the specific frequency band that is output by the LPF 54B is divided by the absolute value intensity $R'_{noise}$ of the R signal in the specific frequency band that is output by the LPF 54A.

The multiplier 57 multiplies the signal component of the R signal in the pulse wave frequency band that is output from the BPF 56A by the weight coefficient a calculated by the calculator 55.

The arithmetic unit 58 executes arithmetic operation "$a*R_{signal}-G_{signal}$" in which the signal component of the G signal in the pulse wave frequency band that is output from the BPF 56B is subtracted from the signal component of the R signal in the pulse wave frequency band that is multiplied by the weight coefficient a by the multiplier 57. The time-series data of the signal obtained by the arithmetic operation corresponds to the heart beat waveform.

The detector 59 detects the subject's pulse waves using the signal after the arithmetic operation. As a form, the detector 59 outputs the time-series data of the signal as a pulse wave detection result. As another form, the detector 59 may detect the heart rate by applying Fourier transform to the time-series data of the signal.

Figure 8:
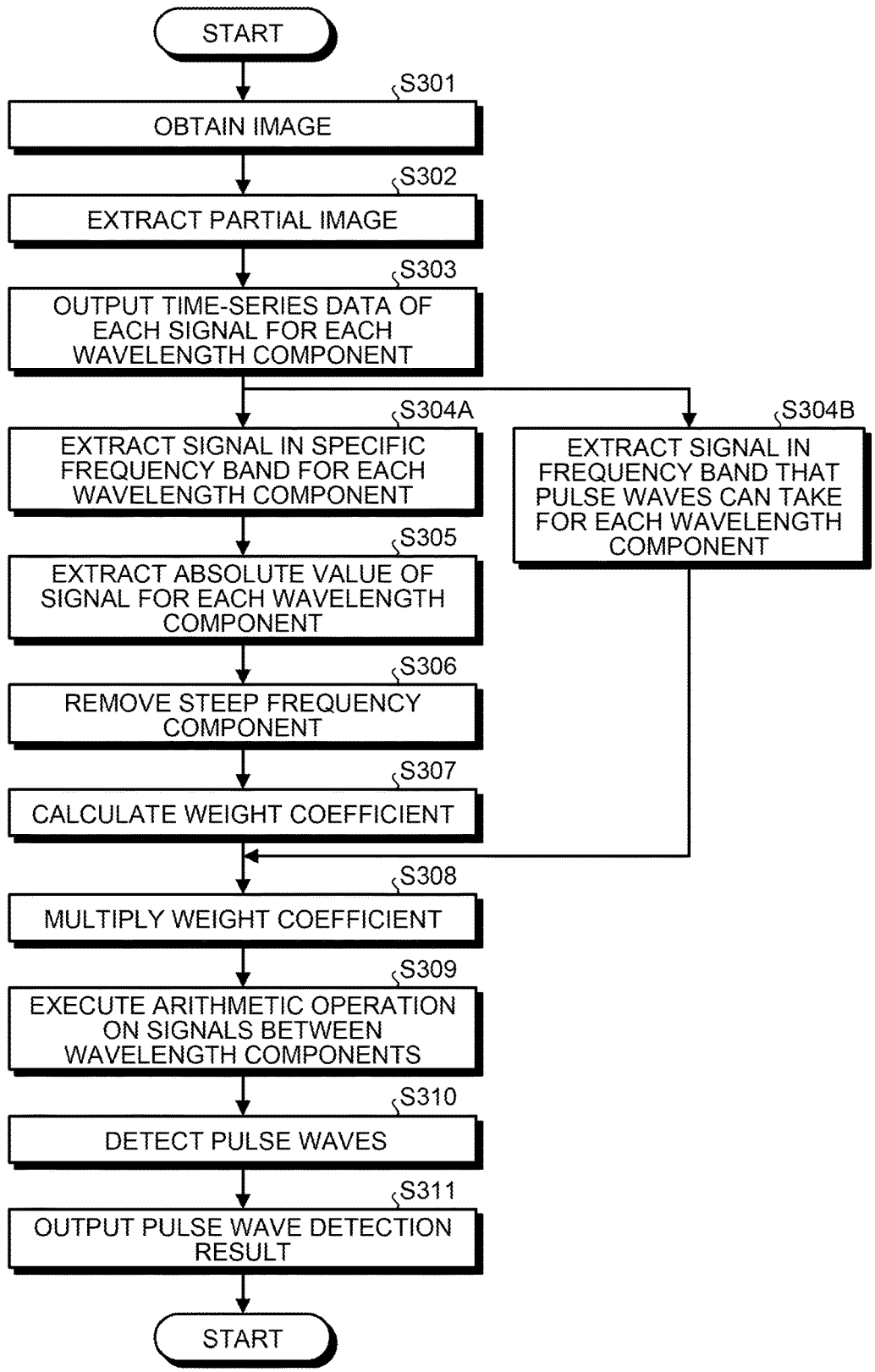
FIG. 8 is a flowchart illustrating procedures of detection process according to the second embodiment.

FIG. 8 is a flowchart illustrating procedures of detection process according to the second embodiment. As illustrated in FIG. 8, when an image including the subject is obtained (Step S301), the obtaining unit 51 extracts a predetermined facial part, such as a partial image including the subject's nose serving as a basis, from the image obtained at Step S301 (Step S302).

Next, the obtaining unit 51 outputs time-series data of the R signal to the BPF 52A and the BPF 56A, and outputs time-series data of the G signal to the BPF 52B and the BPF 56B (Step S303).

Next, the BPF 52A extracts a signal component of the R signal in the specific frequency band, for example, the signal component in the frequency band equal to or larger than 3 bpm and less than 20 bpm and the BPF 52B extracts the signal component of the G signal in the specific frequency band (Step S304A).

Thereafter, the extracting unit 53A extracts the absolute intensity value of the signal component of the R signal in the specific frequency band, and the extracting unit 53B extracts the absolute intensity value of the signal component of the G signal in the specific frequency band (Step S305).

Thereafter, the LPF 54A removes a steep frequency component from the time-series data of the absolute intensity value of the R signal in the specific frequency band, and the LPF 54B removes a steep frequency component from the time-series data of the absolute intensity value of the G signal in the specific frequency band (Step S306).

Next, the calculator 55 calculates the weight coefficient a by executing the division "$G'_{noise}/R'_{noise}$" in which the absolute value intensity $G'_{noise}$ of the G signal in the specific frequency band that is output by the LPF 54B is divided by the absolute value intensity $R'_{noise}$ of the R signal in the specific frequency band that is output by the LPF 54A (Step S307).

In parallel with the processing at the above step S304A, the BPF 56A extracts a signal component of the R signal in the pulse wave frequency band, for example, the frequency band equal to or larger than 42 bpm and less than 240 bpm, and the BPF 56B extracts a signal component of the G signal in the pulse wave frequency band (Step S304B).

Thereafter, the multiplier 57 multiplies the signal component of the R signal in the pulse wave frequency band that is extracted at Step S304B by the weight coefficient a calculated at step S307 (Step S308). Next, the arithmetic unit 58 executes the arithmetic operation "$a*R_{signal}-G_{signal}$" in which the signal component of the G signal in the pulse wave frequency band that has been extracted at Step S304B is subtracted from the signal component of the R signal in the pulse wave frequency band that has been multiplied by the weight coefficient a at Step S308 (Step S309).

Next, the detector 59 detects the subject's pulse waves, such as the heart rate and the heart beat waveform, using the time-series data of the signal after the arithmetic operation (Step S310), outputs the pulse wave detection result to the client terminal 30 (Step S311), and ends the process.

Effects of Second Embodiment

As described above, the server apparatus 50 according to the present embodiment cancels the noise component in the time-series space, to detect pulse waves. This case also enables reduction in the calculation quantity of the weight coefficient like the first embodiment described above; hence this case suppresses an increase in processing load or a decrease in accuracy when the noise is reduced. In addition, because the server apparatus 50 according to the present embodiment enables obtaining of the heart beat waveform serving as a form of pulse waves without Fourier transform, in comparison with the first embodiment described above, the server apparatus 50 more effectively suppresses an increase in processing load or a decrease in accuracy.

Figure 9:
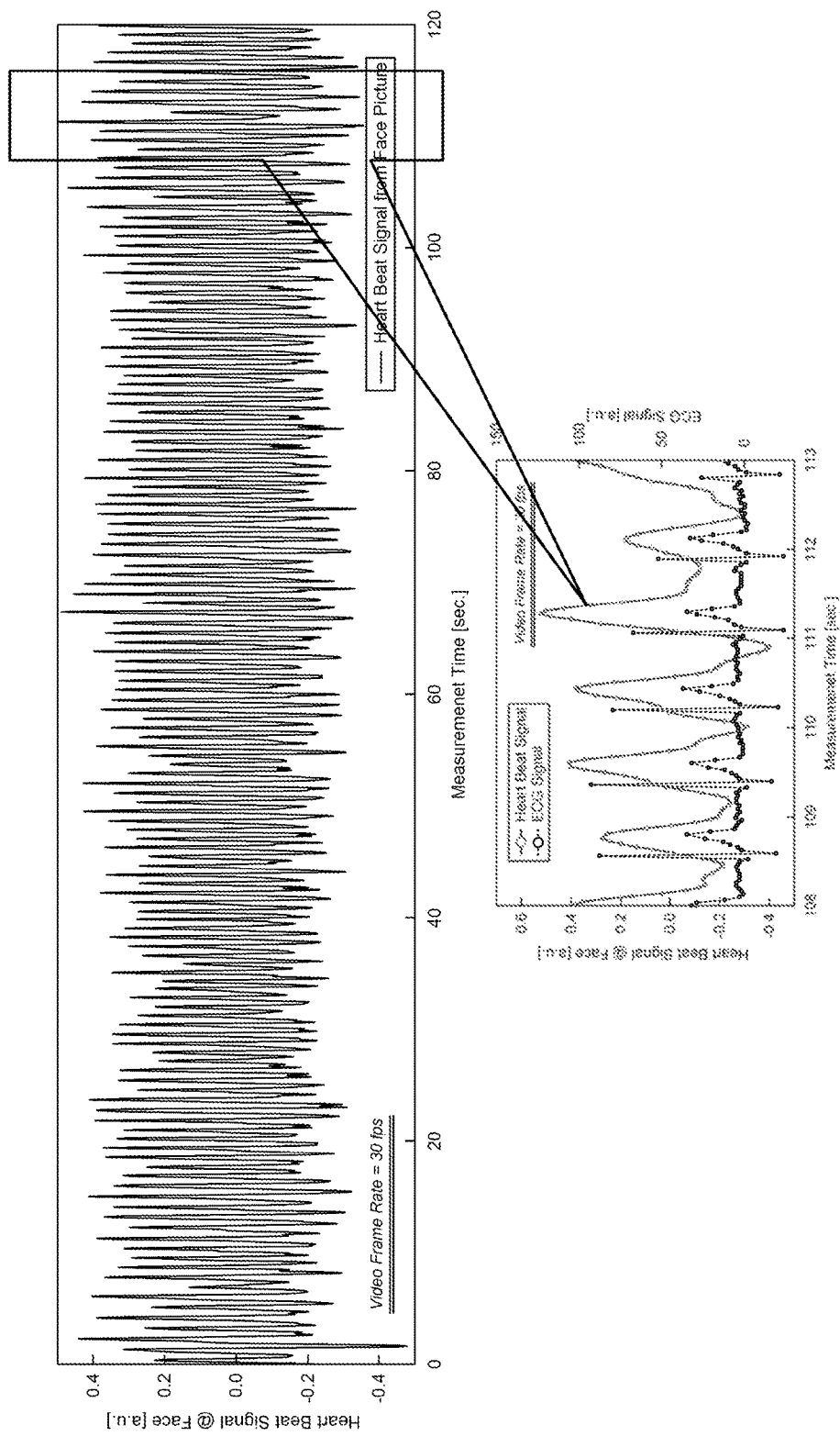
FIG. 9 is a diagram illustrating an example of comparison between a pulse wave detection result according to the second embodiment and a reference of an ECG.

FIG. 9 is a diagram illustrating an example of comparison between the pulse wave detection result according to the second embodiment and the reference. The reference in FIG. 9 illustrates an electrocardiogram (ECG) measured by electrocardiography. The vertical axis of the graph illustrated in FIG. 9 indicates the signal amplitude, and the horizontal axis indicates the time (sec). As illustrated in FIG. 9, the time-series data of the signal after arithmetic operation performed by the arithmetic unit 58 has peaks located in positions substantially identical with the positions of the peaks of the ECG waveform of the reference, and they can be regarded as having relation substantially similar to each other. This comparison indicates that detection of pulse waves by cancelling the noise component in the time-series space can achieve pulse wave detection accuracy that is not inferior to that of the ECG waveform of the reference.

Third Embodiment

The present invention may be carried out in various different forms as well as the embodiments described above relating to the disclosed apparatus. The following is explanation of other embodiments included in the present invention.

Although the first embodiment and the second embodiment described above illustrate the case of using two types of input signals, that is, the R signal and the G signal, signals of desired types and a desired number may be used as the input signals, as long as the signals have different light wavelength components. For example, a combination of two signals may be used among signals of different light wavelength components, such as R, G, B, IR, and NIR, or a combination of three or more signals may be used.

Distribution and Integration

In addition, it is noted that the components of each device illustrated in the description of the foregoing embodiments may not necessarily be physically configured as illustrated in the drawings. That is, specific manners of distribution and integration of the devices are not limited to those illustrated in the drawings and the whole or part thereof may be distributed or integrated functionally or physically in any units depending on various loads and use conditions. For example, the client terminal 30 may be operated in a stand-alone manner by causing the client terminal 30 to execute a pulse wave detection program that executes processing corresponding to that executed by the functional units of the server apparatus 10, such as the obtaining unit 12, the converting unit 13, the extracting unit 14, the calculator 15, the multiplier 16, the arithmetic unit 17, and the detector 18. In addition, among the obtaining unit 12, the converting unit 13, the extracting unit 14, the calculator 15, the multiplier 16, the arithmetic unit 17, and the detector 18, part of the functional units may be connected via a network as an external device of the server apparatus 10. For example, because arithmetic operation such as DFT incurs high processing load, the converting unit 13 may be mounted on the client terminal 30, and the other functional units may be mounted on the server apparatus 10, from the viewpoint of causing the server apparatus 10 having high specifications between the client and the server to perform the process. Besides, the function of the above server apparatus 10 may be achieved by separate devices including part of the functional units among the obtaining unit 12, the converting unit 13, the extracting unit 14, the calculator 15, the multiplier 16, the arithmetic unit 17, and the detector 18 and connected via a network to cooperate with each other.

Pulse Wave Detection Program

The above processes explained in the above embodiments can be implemented by executing a computer program prepared in advance by a computer such as a personal computer and a workstation. The following is explanation of an example of a computer that executes a pulse wave detection program having the same function as that in the above embodiments, with reference to FIG. 10.

Figure 10:
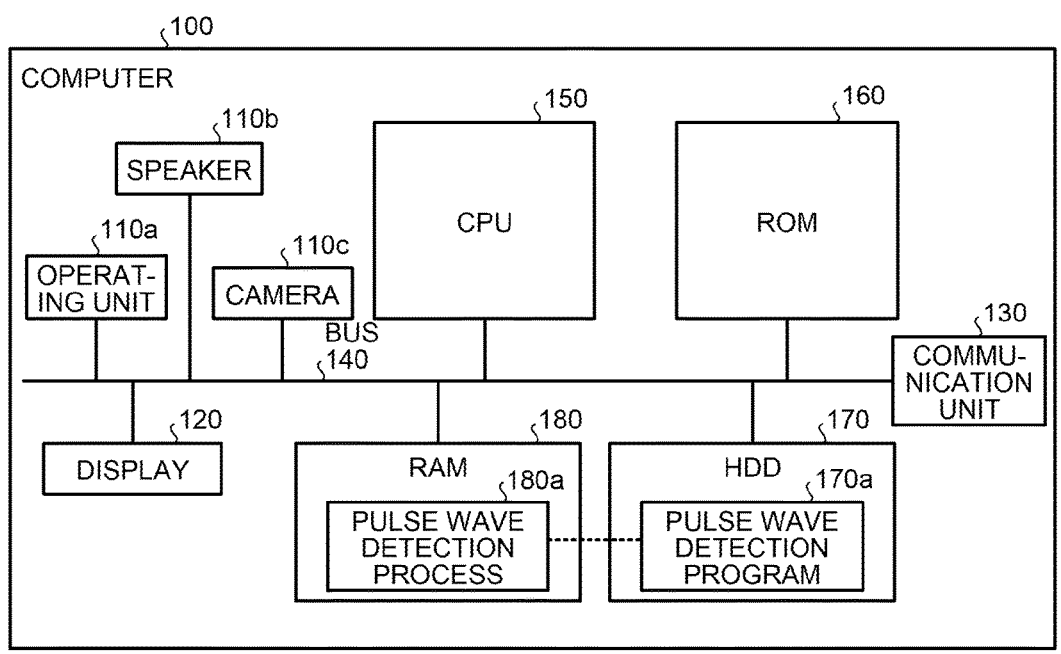
FIG. 10 is a diagram for explaining an example of a computer that executes the pulse wave detection program according to the first embodiment to a third embodiment.

FIG. 10 is a diagram for explaining an example of the computer that executes the pulse wave detection program according to the first embodiment to the third embodiment. As illustrated in FIG. 10, a computer 100 includes an operating unit 110*a*, a speaker 110*b*, a camera 110*c*, a display 120, and a communication unit 130. The computer 100 also includes a central processing unit (CPU) 150, a read-only memory (ROM) 160, a hard disk drive (HDD) 170, and a random access memory (RAM) 180. The units 110 to 180 are connected via a bus 140.

As illustrated in FIG. 10, the HDD 170 stores therein in advance a pulse wave detection program 170*a* that has functions similar to those of the obtaining unit 12, the converting unit 13, the extracting unit 14, the calculator 15, the multiplier 16, the arithmetic unit 17, and the detector 18 illustrated in the first embodiment described above. The pulse wave detection program 170*a* may be properly integrated or distributed in the same manner as the constituent elements of the functional units illustrated in FIG. 1 and FIG. 7. Specifically, all pieces of data stored in the HDD 170 are not necessarily stored in the HDD 170, but only data for the process may be stored in the HDD 170.

Next, the CPU 150 reads out the pulse wave detection program 170*a* from the HDD 170, to expand the pulse wave detection program 170*a* in the RAM 180. In this manner, the pulse wave detection program 170*a* functions as a pulse wave detection process 180*a*, as illustrated in FIG. 10. The pulse wave detection process 180*a* properly expands various pieces of data read out of the HDD 170 in regions assigned thereto on the RAM 180, to execute various processes based on the expanded various pieces of data. The pulse wave detection process 180*a* includes processes executed by the functional units illustrated in FIG. 1 or FIG. 7, for example, the processes illustrated in FIG. 6 and FIG. 8. All the processors that are virtually implemented on the CPU 150 do not necessarily operate on the CPU 150, but only processors for the process may be virtually implemented.

The above pulse wave detection program 170*a* is not necessarily stored in the HDD 170 or the ROM 160 initially. For example, each program may be stored in a "portable physical medium" that is inserted into the computer 100, such as a flexible disk (FD), a compact disc read only memory (CD-ROM), a digital versatile disc (DVD), a magneto-optical disc, and an integrated circuit (IC) card. The computer 100 may obtain and execute each program from the portable physical medium. Otherwise, each program may be stored in another computer or a server apparatus that is connected to the computer 100 via a public line, the Internet, a LAN, or a wide area network (WAN), and the computer 100 may obtain and execute each program therefrom.

The pulse wave detection method disclosed in the present application produces the effect of suppressing an increase in processing load or a decrease in accuracy in reduction of noise.

All examples and conditional language recited herein are intended for pedagogical purposes of aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although the embodiments of the present invention have been described in detail, it should be understood that the various changes, substitutions, and alterations could be made hereto without departing from the spirit and scope of the invention.

What is claimed is:

1. A pulse wave detection method comprising:
    obtaining images obtained by photographing a subject with an imaging device;
    extracting intensities representative of signal components of a specific frequency band for respective wavelength components among signals of a plurality of wavelength components included in the images, the specific frequency band having a frequency band to which pulse waves do not correspond, and having a section having less than or equal to a predetermined length overlapping a frequency band that the pulse waves are enabled to take;
    calculating, using the intensities extracted for the respective wavelength components, a weight coefficient by which a signal is multiplied when the signals are calculated between the wavelength components to minimize an arithmetic value of the signal components in the specific frequency band after multiplication;
    multiplying at least one of the signals of the respective wavelength components by the weight coefficient;

performing arithmetic operation on the signals between the wavelength components after multiplication by the weight coefficient; and detecting pulse waves of the subject using a signal after the arithmetic operation to enable suppression of an increase in processing load or a decrease in accuracy when noise is reduced, wherein the extracting includes first extracting the signal components of the specific frequency band for the respective wavelength components from the signals of the respective wavelength components using a low-pass filter or a band-pass filter and second extracting signal components of the frequency band that the pulse waves are enabled to take for the respective wavelength components from the signals of the respective wavelength components using a band-pass filter, the calculating includes calculating the weight coefficient using the intensities of the signal components of the specific frequency band, the signal components being extracted for the respective wavelength components, the multiplying includes multiplying the signal components of the frequency band that the pulse waves are enabled to take by the weight coefficient, the performing includes performing arithmetic operation on the signal components of the frequency band that the pulse waves are enabled to take between the wavelength components after multiplication by the weight coefficient, and the detecting includes detecting the pulse waves of the subject using a signal waveform after the arithmetic operation, wherein the first extracting includes extracting absolute intensity values in the specific frequency band that are extracted for the respective wavelength components, and the calculating includes calculating the weight coefficient by calculating a ratio of the absolute intensity values between the wavelength components, wherein the first extracting includes extracting the absolute intensity value of the signal component of the specific frequency band, by executing a multiplication process of exponentiating the signal component of an R component in the specific frequency band, and extracting the absolute intensity value of the signal component of the specific frequency band, by executing a multiplication process of exponentiating the signal component of a G component in the specific frequency band, wherein the pulse wave detection method further includes executing smoothing on time-series data of the absolute intensity value in the specific frequency band to respond to time change.

2. The pulse wave detection method according to claim 1, further comprising:

converting the signals of the respective wavelength components into frequency components, wherein the multiplying includes multiplying one of spectrums obtained by converting the signals of the wavelength components into the frequency components by the weight coefficient, the performing includes performing arithmetic operation of the spectrums between the wavelength components after multiplication by the weight coefficient, and the detecting includes detecting the pulse waves of the subject using a spectrum after the arithmetic operation.

3. The pulse wave detection method according to claim 2, wherein the extracting includes extracting an average power intensity of the specific frequency band from the spectrums obtained by converting the signals of the respective wavelength components into the frequency components, and the calculating includes calculating the weight coefficient by calculating a ratio of the average power intensity between the wavelength components.

4. The pulse wave detection method according to claim 1, wherein the signals include two or more wavelengths, and include different light absorption sensitivities to hemoglobin.

5. The pulse wave detection method according to claim 4, wherein at least one signal among the signals of the wavelength components is a signal having a band based on a light wavelength of 525 nm, and the other signals are signals having bands of light wavelengths other than the band.

6. The pulse wave detection method according to claim 1, wherein signal components less than 1 Hz are used as the signal components of the specific frequency band.

7. The pulse wave detection method according to claim 1, wherein the detecting includes, when canceling a noise component in a time-series space to detect pulse waves, obtaining a heart beat waveform serving as a form of pulse waves without Fourier transform.

8. The pulse wave detection method according to claim 1, wherein the time-series data of a signal after arithmetic operation has peaks located in positions substantially identical with positions of peaks of an electrocardiogram waveform of a reference, and they have relation substantially similar to each other.

9. A pulse wave detection apparatus comprising:

a processor configured to:

obtain images obtained by photographing a subject with an imaging device;

extract intensities representative of signal components of a specific frequency band for respective wavelength components among signals of a plurality of wavelength components included in the images, the specific frequency band having a frequency band to which pulse waves do not correspond, and having a section having less than or equal to a predetermined length overlapping a frequency band that the pulse waves are enabled to take;

calculate, using the intensities extracted for the respective wavelength components, a weight coefficient by which a signal is multiplied when the signals are calculated between the wavelength components to minimize an arithmetic value of the signal components in the specific frequency band after multiplication;

multiply at least one of the signals of the respective wavelength components by the weight coefficient;

perform arithmetic operation on the signals between the wavelength components after multiplication by the weight coefficient; and detect pulse waves of the subject using a signal after the arithmetic operation to enable suppression of an increase in processing load or a decrease in accuracy when noise is reduced, wherein the extracting includes first extracting the signal components of the specific frequency band for the respective wavelength components from the signals of the respective wavelength components using a low-pass filter or a band-pass filter and second extracting signal components of the frequency band that the pulse waves are enabled to take for the respective wavelength components from the signals of the respective wavelength components using a band-pass filter, the calculating includes calculating the weight coefficient using the intensities of the signal components of the specific frequency band, the signal components being extracted for the respective wavelength components, the multiplying includes multiplying the signal components of the frequency band that the pulse waves are enabled to take by the weight coefficient, the performing includes performing arithmetic operation on the signal components of the frequency band that the pulse waves are enabled to take between the wavelength components after multiplication by the weight coefficient, and the detecting includes detecting the pulse waves of the subject using a signal waveform after the arithmetic operation, wherein the first extracting includes extracting absolute intensity values in the specific frequency band that are extracted for the respective wavelength components, and the calculating includes calculating the weight coefficient by calculating a ratio of the absolute intensity values between the wavelength components, wherein the first extracting includes extracting the absolute intensity value of the signal component of the specific frequency band, by executing a multiplication process of exponentiating the signal component of an R component in the specific frequency band, and extracting the absolute intensity value of the signal component of the specific frequency band, by executing a multiplication process of exponentiating the signal component of a G component in the specific frequency band, wherein the processor is further configured to execute smoothing on time-series data of the absolute intensity value in the specific frequency band to respond to time change.

10. A non-transitory computer readable recording medium having stored therein a pulse wave detection program that causes a computer to execute a process comprising:

obtaining images obtained by photographing a subject with an imaging device;

extracting intensities representative of signal components of a specific frequency band for respective wavelength components among signals of a plurality of wavelength components included in the images, the specific frequency band having a frequency band to which pulse waves do not correspond, and having a section having less than or equal to a predetermined length overlapping a frequency band that the pulse waves are enabled to take;

calculating, using the intensities extracted for the respective wavelength components, a weight coefficient by which a signal is multiplied when the signals are calculated between the wavelength components to minimize an arithmetic value of the signal components in the specific frequency band after multiplication;

multiplying at least one of the signals of the respective wavelength components by the weight coefficient;

performing arithmetic operation on the signals between the wavelength components after multiplication by the weight coefficient; and detecting pulse waves of the subject using a signal after the arithmetic operation to enable suppression of an increase in processing load or a decrease in accuracy when noise is reduced, wherein the extracting includes first extracting the signal components of the specific frequency band for the respective wavelength components from the signals of the respective wavelength components using a low-pass filter or a band-pass filter and second extracting signal components of the frequency band that the pulse waves are enabled to take for the respective wavelength components from the signals of the respective wavelength components using a band-pass filter, the calculating includes calculating the weight coefficient using the intensities of the signal components of the specific frequency band, the signal components being extracted for the respective wavelength components, the multiplying includes multiplying the signal components of the frequency band that the pulse waves are enabled to take by the weight coefficient, the performing includes performing arithmetic operation on the signal components of the frequency band that the pulse waves are enabled to take between the wavelength components after multiplication by the weight coefficient, and the detecting includes detecting the pulse waves of the subject using a signal waveform after the arithmetic operation, wherein the first extracting includes extracting absolute intensity values in the specific frequency band that are extracted for the respective wavelength components, and the calculating includes calculating the weight coefficient by calculating a ratio of the absolute intensity values between the wavelength components, wherein the first extracting includes extracting the absolute intensity value of the signal component of the specific frequency band, by executing a multiplication process of exponentiating the signal component of an R component in the specific frequency band, and extracting the absolute intensity value of the signal component of the specific frequency band, by executing a multiplication process of exponentiating the signal component of a G component in the specific frequency band, wherein the process further includes executing smoothing on time-series data of the absolute intensity value in the specific frequency band to respond to time change.

* * * * *